(12) United States Patent
Le et al.

(10) Patent No.: US 12,290,265 B2
(45) Date of Patent: May 6, 2025

(54) OPTIMIZED DETACHMENT SYSTEMS BASED ON LEVERAGE FROM ELECTRICAL LOCUS TARGETING AND RELATED MEDICAL DEVICES

(71) Applicant: Balt USA, LLC, Irvine, CA (US)

(72) Inventors: Nguyen Le, Foothill Ranch, CA (US); Dawson Le, Garden Grove, CA (US); Randall Takahashi, Mission Viejo, CA (US)

(73) Assignee: BALT USA, LLC, Irvine, CA (US)

( * ) Notice: Subject to any disclaimer, the term of this patent is extended or adjusted under 35 U.S.C. 154(b) by 0 days.

(21) Appl. No.: 17/601,416

(22) PCT Filed: Apr. 2, 2020

(86) PCT No.: PCT/US2020/026426
§ 371 (c)(1),
(2) Date: Oct. 4, 2021

(87) PCT Pub. No.: WO2020/206147
PCT Pub. Date: Oct. 8, 2020

(65) Prior Publication Data
US 2022/0202424 A1   Jun. 30, 2022

Related U.S. Application Data

(60) Provisional application No. 62/830,334, filed on Apr. 5, 2019.

(51) Int. Cl.
*A61B 17/12* (2006.01)
*A61B 17/00* (2006.01)

(52) U.S. Cl.
CPC .. *A61B 17/12113* (2013.01); *A61B 17/12145* (2013.01); *A61B 17/12154* (2013.01);
(Continued)

(58) Field of Classification Search
CPC ........ A61B 17/12113; A61B 17/12145; A61B 17/12154; A61B 2017/00526;
(Continued)

(56) References Cited

U.S. PATENT DOCUMENTS 3,226,806 A * 1/1966 Clyde ................. H01J 9/08
427/427
5,250,071 A 10/1993 Palermo
(Continued)

FOREIGN PATENT DOCUMENTS

EP          3035867 B1    6/2016
KR    1020100111606 B1   10/2010
(Continued)

OTHER PUBLICATIONS

"The Inductor," Electronic Tutorials [online] https://web.archive.org/web/20170707200019/http://www.electronics-tutorials.ws/inductor/inductor.html.
(Continued)

*Primary Examiner* — Lawrence Averick
(74) *Attorney, Agent, or Firm* — THE MARBURY LAW GROUP, PLLC

(57) ABSTRACT

Improved thermal detachment driven by leverage from: improved electrical locus targeting allows electron density to define Optimal Regions balancing the resistance and heat whereby, detachment systems are shifted and realigned coaxially and placed closer to the ends of subject coils while being hermetically sealed, manufacturing steps are taught, to show how system is made.

4 Claims, 10 Drawing Sheets

(52) U.S. Cl.
CPC .............. *A61B 2017/00526* (2013.01); *A61B 2017/12068* (2013.01)

(58) Field of Classification Search
CPC .... A61B 2017/12068; A61B 17/12022; H05B 3/00; H05B 6/1245; H05B 6/36; H05B 6/44; H05B 2206/024
See application file for complete search history.

(56) References Cited

U.S. PATENT DOCUMENTS

| | | | |
|---|---|---|---|
| 5,354,295 | A | 10/1994 | Guglielmi et al. |
| 5,895,391 | A | 4/1999 | Farnholtz |
| 5,989,242 | A | 11/1999 | Saadat et al. |
| 6,468,266 | B1 | 10/2002 | Bashiri et al. |
| 6,605,101 | B1 | 8/2003 | Schaefer et al. |
| 6,660,020 | B2 | 12/2003 | Wallace et al. |
| 6,884,974 | B2 * | 4/2005 | Howard .................. H05B 3/16 219/532 |
| 7,608,089 | B2 | 10/2009 | Wallace et al. |
| 7,708,755 | B2 | 5/2010 | Davis, III et al. |
| 7,819,892 | B2 | 10/2010 | Balgobin et al. |
| 8,066,036 | B2 | 11/2011 | Monetti et al. |
| 8,192,480 | B2 | 6/2012 | Tieu et al. |
| 8,273,100 | B2 | 9/2012 | Martinez |
| 8,425,550 | B2 | 4/2013 | Elliott et al. |
| 9,011,480 | B2 | 4/2015 | Divino et al. |
| 9,242,070 | B2 | 1/2016 | Tieu |
| 10,426,485 | B2 | 10/2019 | Lorenzo |
| 10,426,486 | B2 | 10/2019 | Guo et al. |
| 10,478,192 | B2 | 11/2019 | Teoh et al. |
| 10,492,793 | B2 | 12/2019 | Elliott |
| 10,537,333 | B2 | 1/2020 | Teoh et al. |
| 10,542,995 | B2 | 1/2020 | Chen et al. |
| 10,548,606 | B2 | 2/2020 | Hui et al. |
| 2004/0182853 | A1 * | 9/2004 | Howard .................. H05B 3/16 219/536 |
| 2006/0122493 | A1 | 6/2006 | Atalar et al. |
| 2007/0055302 | A1 | 3/2007 | Henry et al. |
| 2007/0118172 | A1 | 5/2007 | Balgobin et al. |
| 2007/0223896 | A1 * | 9/2007 | Bents ....................... H05B 3/48 392/472 |
| 2009/0163780 | A1 | 6/2009 | Tieu |
| 2012/0065660 | A1 | 3/2012 | Ferrera et al. |
| 2012/0209310 | A1 | 8/2012 | Chen et al. |
| 2013/0331883 | A1 | 12/2013 | Strauss et al. |
| 2014/0214159 | A1 | 7/2014 | Vidlund et al. |
| 2015/0057700 | A1 | 2/2015 | Chen et al. |
| 2015/0289879 | A1 | 10/2015 | Bowman |
| 2016/0100819 | A1 | 4/2016 | Tieu |
| 2017/0319826 | A1 | 11/2017 | Bowman et al. |
| 2018/0271533 | A1 | 9/2018 | Le et al. |
| 2021/0007750 | A1 | 1/2021 | Le et al. |

FOREIGN PATENT DOCUMENTS

| | | | |
|---|---|---|---|
| WO | 99/22651 | A1 | 5/1999 |
| WO | 2008144587 | A2 | 11/2008 |
| WO | 2015-095360 | A1 | 6/2015 |
| WO | 2017105479 | A1 | 6/2017 |
| WO | 2018129478 | A1 | 7/2018 |

OTHER PUBLICATIONS

Korean Intellectual Property Office, "International Search Report and Written Opinion," issued in related International Patent Application PCT/US2020/026426, mailed Jul. 24, 2020 (11 pages).
Korean Intellectual Property Office, "International Preliminary Report on Patentability," issued in related International Patent Application PCT/US2020/026426, issued on Sep. 28, 2021 (8 pages).
The International Bureau of WIPO, "International Preliminary Report on Patentability," issued in related International Patent Application No. PCT/US2020/026426, dated Sep. 28, 2021 (8 pages).
Korean Intellectual Property Office, "International Search Report and Written Opinion," issued in related International Patent Application No. PCT/US2020/026426, mailed Jul. 24, 2020 (11 pages).
Balt USA, "Optimax Delivers Volume," Optima™ Coil System Product Marketing Publication for Optima Complex 18, MKTG-200 Rev. A (2020) 3 pages.
Balt USA, "Optima™ Coil System Delivers," Optima™ Coil System Product Marketing Pamphlet, MKTG-165 Rev. A (2019) 2 pages.
Korean Intellectual Property Office, "International Preliminary Report on Patentability," issued in related International Patent Application No. PCT/US2018/012838 dated Jul. 9, 2019 (11 pages).
Korean Intellectual Property Office, "International Search Report and Written Opinion," issued in related International Patent Application No. PCT/US2018/012838 mailed May 2, 2018 (17 pages).
Korean Intellectual Property Office, "International Search Report and Written Opinion," issued in related International Patent Application No. PCT/US2015/066605 mailed Aug. 18, 2016 (15 pages).
Korean Intellectual Property Office, "International Preliminary Report on Patentability," issued in related International Patent Application No. PCT/US2015/066605 mailed Jun. 19, 2018 (11 pages).
Korean Intellectual Property Office, "International Search Report and Written Opinion," issued in related International Patent Application No. PCT/US2014/070908 mailed Apr. 3, 2015 (14 pages).
Korean Intellectual Property Office, "International Preliminary Report on Patentability," issued in related International Patent Application No. PCT/US2014/070908 dated Jun. 21, 2016 (11 pages).
European Patent Office, "Extended European Search Report," issued in related European Patent Application No. 18736066.4 dated Nov. 6, 2020 (12 pages).
European Patent Office, "Partial Supplementary European Search Report," issued in related European Patent Application No. 18736066.4 dated Aug. 3, 2020 (14 pages).
U.S. Patent and Trademark Office, "Restriction Requirement," issued in related U.S. Appl. No. 16/476,524 dated Apr. 27, 2021 (9 pages).
U.S. Patent and Trademark Office, "Non-Final Office Action," issued in related U.S. Appl. No. 16/476,524 dated Jul. 16, 2021 (9 pages).
U.S. Patent and Trademark Office, "Final Office Action," issued in related U.S. Appl. No. 16/476,524 dated Feb. 9, 2022 (10 pages).
U.S. Patent and Trademark Office, "Non-final Office Action," issued in related U.S. Appl. No. 15/537,881 dated Apr. 15, 2019 (15 pages).
U.S. Patent and Trademark Office, "Final Office Action," issued in related U.S. Appl. No. 15/537,881 dated Sep. 24, 2019 (15 pages).
U.S. Patent and Trademark Office, "Final Office Action," issued in related U.S. Appl. No. 15/537,881 dated Mar. 30, 2020 (16 pages).
U.S. Patent and Trademark Office, "Advisory Action," issued in related U.S. Appl. No. 15/537,881 dated Oct. 6, 2020 (5 pages).
U.S. Patent and Trademark Office, "Non-Final Office Action," issued in related U.S. Appl. No. 16/927,832 dated Oct. 27, 2021 (13 pages).
U.S. Patent and Trademark Office, "Final Office Action," issued in related U.S. Appl. No. 16/927,832 dated Aug. 11, 2022 (8 pages).

* cited by examiner

REFERENCE: www.electronics.tutorials.ws/induction/induction.html $V_L = -L \frac{di}{dt}$ $\frac{di}{dt}$ is defined as the change in current over time as the current is consistent over the .750s, we can define:

$\frac{di}{dt} = \frac{.238A}{.750S} = .3173 \frac{A}{S}$

For $32\Omega$ $V_L = -L \frac{di}{dt}$ $7.616v = -L(.3173 \frac{A}{S})$ $L = -24H$ For $57\Omega$ $V_L = -L \frac{di}{dt}$ $13.566v = -L(.3173 \frac{A}{S})$ $L = -42.754H$ Put in a circuit is given as $P = VI$ $P: (L \frac{di}{dt}) \times i - \frac{1}{2} L \frac{di^2}{dt} = \frac{di}{dt} (\frac{1}{2} Li^2)$

$$W(i) = \frac{1}{2} Li_{(i)}^2$$

$$W(f) = \frac{1}{2}(24p)(.238A)^2$$

$$W(f) = .67975$$

570

$$W(f) = \frac{1}{2} Li_{(f)}^2$$

$$W(f) = \frac{1}{2} Li_{(f)}^2$$

$$W(f) = \frac{1}{2}(42.75414)(.238a)^2$$

OPTIMIZED DETACHMENT SYSTEMS BASED ON LEVERAGE FROM ELECTRICAL LOCUS TARGETING AND RELATED MEDICAL DEVICES

FIELD OF THE INVENTION

The present disclosures relate to the deployment of devices in the neurovascular and related endovascular access situses within mammals and related species, models, robots and computer or AI generated simulacra of the same.

BACKGROUND OF THE DISCLOSURES

Detachment of, for example, coils and related systems within the cerebral neurovascular space is fraught with issues and challenges.

OBJECTS AND SUMMARY OF THE INVENTION

Briefly stated, improved thermal detachment driven by leverage from improved electrical locus targeting and related applications of the same allows electron density to define Optimal Regions balancing the resistance and heat whereby, for example OPTIMA® brands of coils (BALT USA®, Orange County, CA) and their detachment systems are from shifted coaxially and placed closer to the ends of subject coils.

According to embodiments, there is disclosed a novel combination, of design steps, namely, mapping the precise zone, or locus where a beater coil becomes most heated, frame-shifting said locus to a proximal portion of said coil, severing a requisite "stretch resistance" (SR) thread, closer to the front than conventional systems, and reducing or eliminating any dragger or tail region based upon said frame shifting, As known to those skilled in the Art of neurovascular and neuro-endovascular surgery, inter alia.

According to embodiments, there is disclosed a system, further comprising, "Coaxialization" (as defined herein) of the frame shifted locus within said coil.

According to embodiments, there is disclosed a system of the instant disclosure in total, wherein, any mushroom or the-like shaped artifacts within subject marker bands are mitigated, reduced or eliminated. A process for manufacturing these devices is presented showing that the heater coil is designed to melt said SR thread allowing the implant to separate from the pusher.

According to embodiments, there is disclosed the system of the OPTIMA® brand of Co-axial Heater Coil (BALT USA, Irvine, Calif. 92618) whereby electrical current is delivered from the XCEL® brand of controller.

According to embodiments, there is disclosed the system the instant disclosure in total, whereby, the solution of coaxializing the detachment end of said coil readers the hottest point at the tip by distal movement and folding.

BRIEF DESCRIPTION OF THE DRAWINGS

Various preferred embodiments are described herein with reference to the drawings in which merely illustrative views are offered for consideration, whereby:

FIG. 4 further details electronic validation of the instant system;

FIG. 5 shows induction, energy stored according to the instant systems as explained herein;

Figure 1:
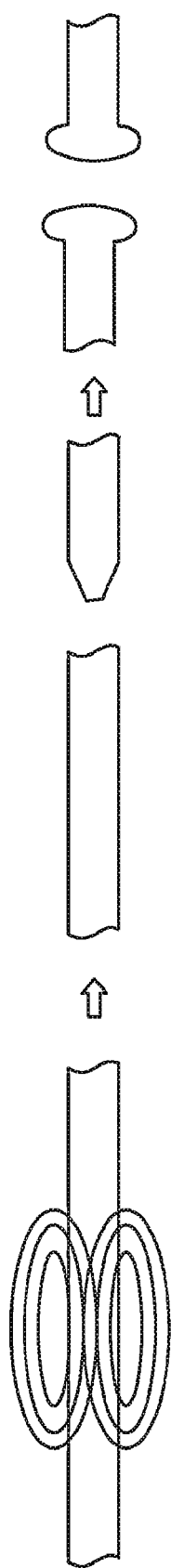
FIG. 1 is a cartoon showing issues addressed and overcome by the present invention.

Corresponding reference characters indicate corresponding components throughout the several views of the drawing. Skilled artisans will appreciate that elements in the figures are illustrated for simplicity and clarity, and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTIONS

The present inventors have realized that optimized mapping of electron density allows them to realize more efficient and reliable detachment among, for example thermal coil detachment systems such as those available (OPTIMA®, BALT USA, Orange County, CA 92618, to treat aneurysms et seq.

Figure 2:
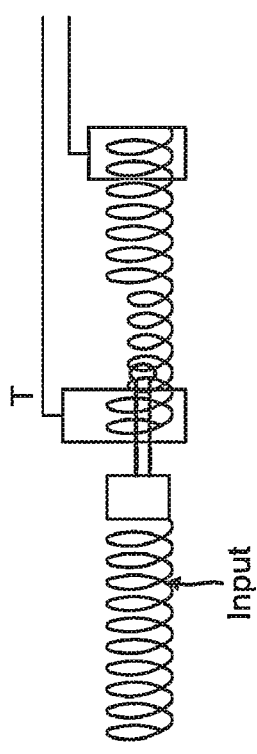
FIG. 2 shows an artefactual element (mushroom-shaped member) as addressed & overcome by the present invention.
Figure 3:
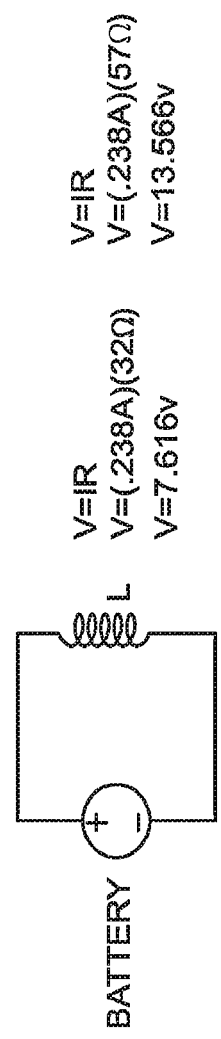
FIG. 3 shows a technical basis for the involved charges.
Figure 6:
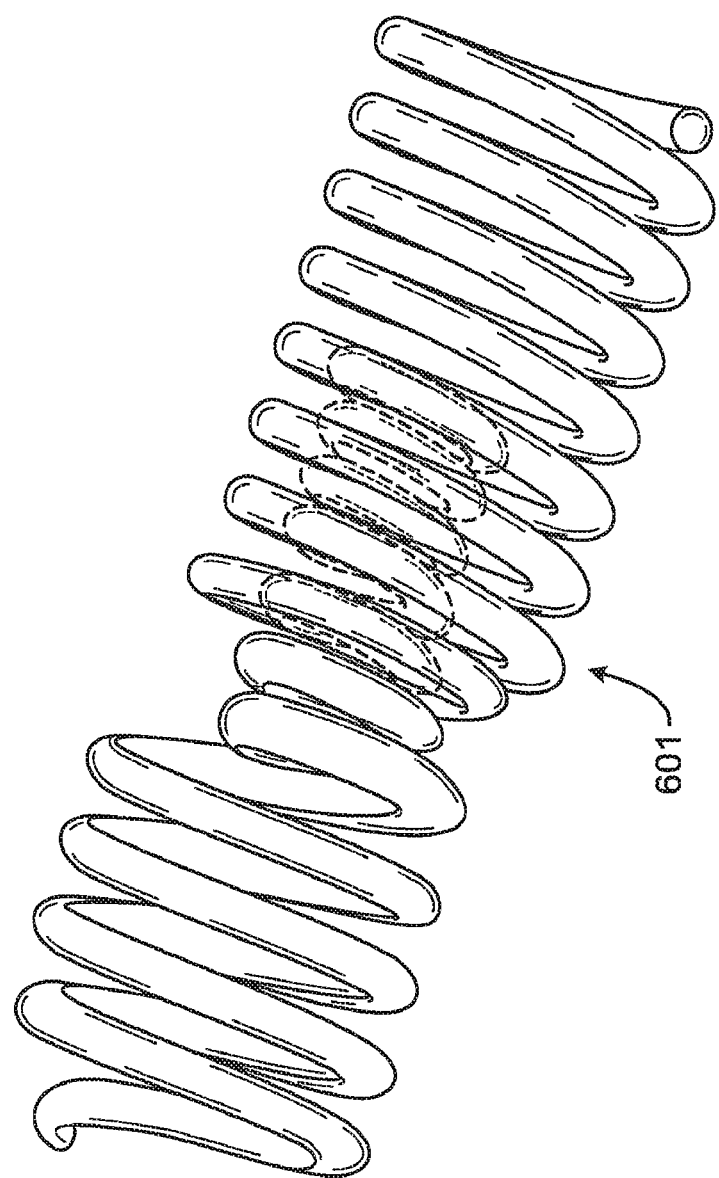
FIG. 6 shows steps in a manufacturing process according to the present invention.

Referring now to FIG. 1-FIG. 13 we see in FIG. 1 how SR thread is disposed with PET followed by the SR thread after heating and generation of "mushroom-shaped members" along with FIG. 2 showing how same mechanically impacts detachment;

FIG. 3 shows electrical equations to the Optima® brand of detachment system, as is self-evident to artisans;

FIG. 4 & FIG. 5 show induction-based calculations and shows how and why power stays constant in the heater coil as it is shifted distally and coaxialized; and FIG. 5 shows induction energy stored according to the instant systems as explained herein.

Figure 7:
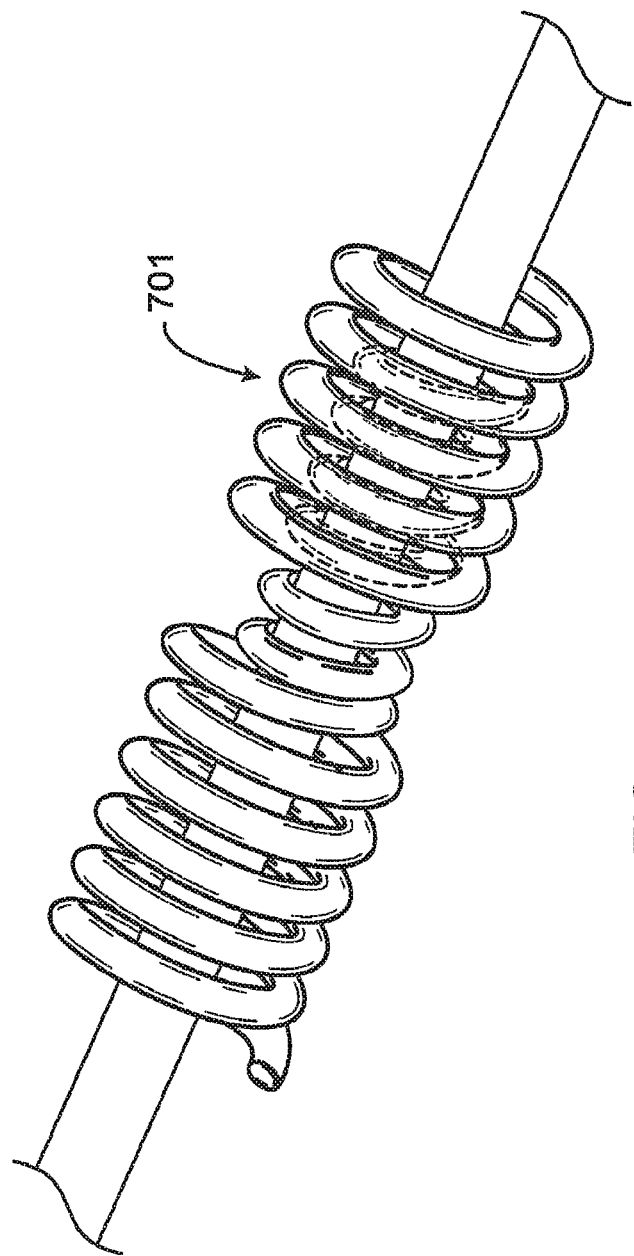
FIG. 7 shows step in a manufacturing process according, to the present invention.
Figure 8:
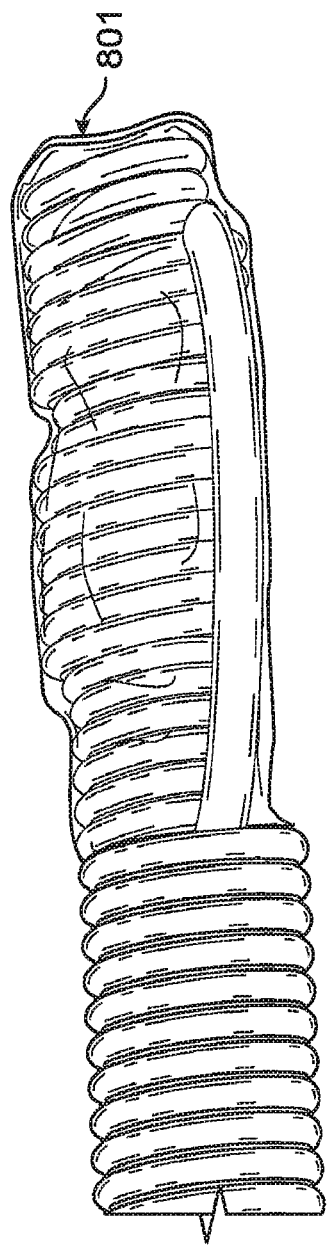
FIG. 8 shows steps in a manufacturing process according to the present invention.
Figure 9:
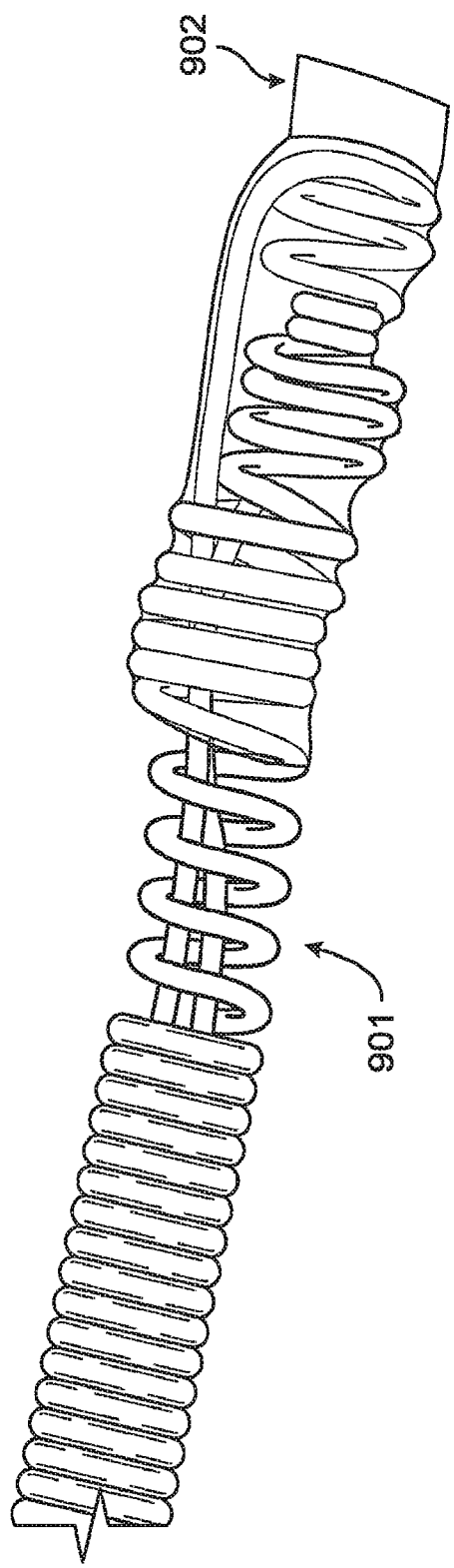
FIG. 9 shows steps in a manufacturing process according to the present invention.
Figure 10:
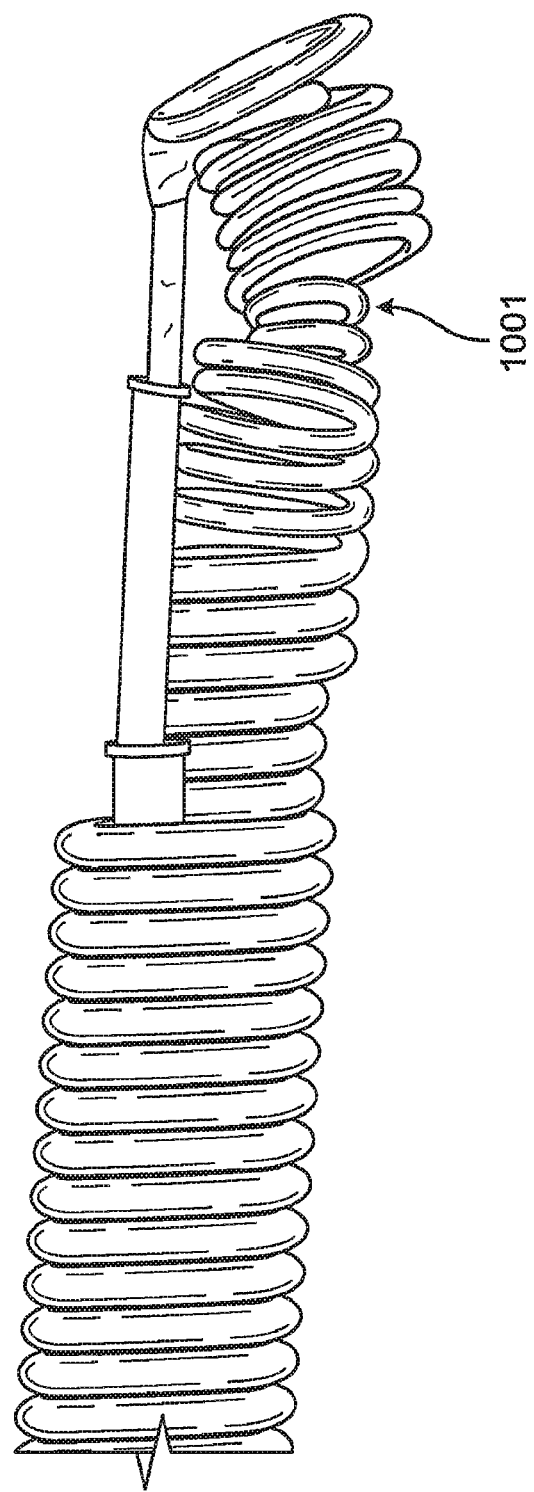
FIG. 10 shows steps in a manufacturing process according to the present invention.
Figure 11:
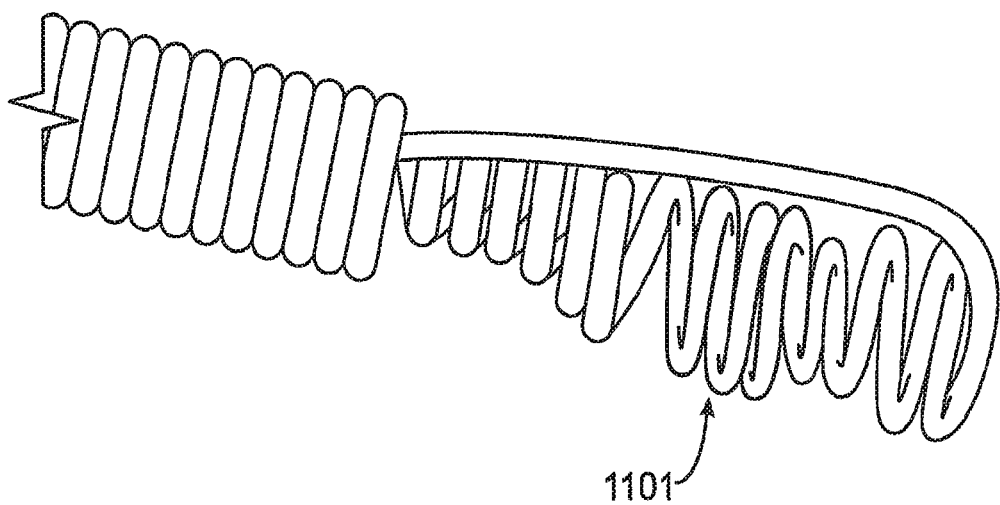
FIG. 11 is prior art heater coil.
Figure 12:
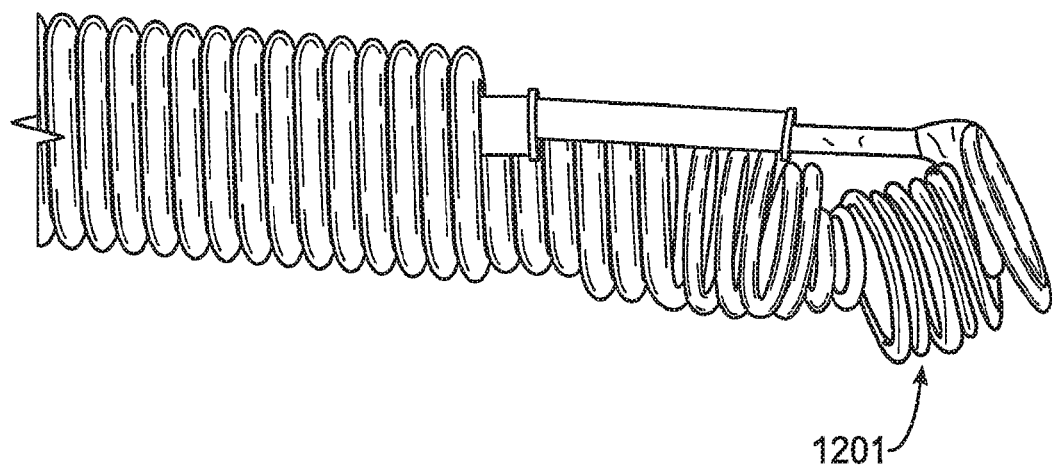
FIG. 12. shows the rotatory coil of the present invention with heat at distal and, according to the present invention.

FIG. 6-FIG. 12 demonstrate embodiments of the improved heater coil principle of operation of the present invention. Heretofore, reliability of detachment was challenged. Namely, first button detachment—defined herein for this application as meaning the implant separates from pusher on first detachment attempt is ensured according to the instant teachings. Methods, including those claimed are shown in details appreciated by Artisans, for example in FIG. 6, wherein the middle of the heater coil is shown at 601 as pinched to a smaller diameter. FIG. 7 likewise shows distal end of heater pushed over pinched section 701 while FIG. 8 indicated first layer of insulation jacket shrunken over heater coil 801. Referring now to FIG. 9, $2^{nd}$ layer of insulation jacket 901 is shrunken over heater sill, while several gaps are created 902 proximal to heater coil. FIG. 10 shows 1001 heat locus (with insulation jackets removed);

while FIG. 11 shows at center 1101, while the present invention is heated at distal end 1201 of heater coil.

Corresponding reference characters indicate corresponding components throughout the several views of the drawings. Skilled artisans will appreciate that elements in the figures are illustrated for simplicity and clarity, and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that ail parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of, the features shown and described (or portions thereof), and it is recognized that various modifications are possible within the scope of the claims. Accordingly, the claims are intended to cover all such equivalents.

Reference throughout this specification to "one embodiment," "an embodiment," or similar language mans that a particular feature, structure, or characteristic described in connection with the embodiment is included in at least one embodiment of the present invention. Thus, appearances of the phrases "in one embodiment," "in an embodiment," and similar throughout this specification may, but do not necessarily, all refer to the same embodiment.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well-known structures, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps an indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be consulted in light of the number of reported significant digits and by applying ordinary mounting techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. Ail methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

A processor may be provided by one or more processors including, for example, one or more of a single core or multi-core processor (e.g., AMD Phenom II X2, Intel Core Duo, AMD Phenom II X4, Intel Core 5, Intel Core I & Extreme Edition 980X, or Intel Xeon E7-2820).

An I/O mechanism may include a video display unit (e.g., a liquid crystal. display (LCD) or a cathode ray tube (CRT)), an alphanumeric input device (e.g., a keyboard), a cursor control device (e.g. a mouse), a disk drive unit, a signal generation device (e.g., a speaker), an accelerometer, a microphone, a cellular radio frequency antenna, and a network interface device (e.g., a network inter as card (NIC), Wi-Fi card, cellular modem, data jack, Ethernet port, modem jack, HDMI port, mini-HDMI port, USB port), touchscreen (e.g., CRT, LCD, LED, AMOLED, Super AMOLED), pointing device, trackpad, light (e.g., LED), light/image projection device, or a combination thereof.

Memory according to the invention refers to a non-transitory memory which is provided by one or more tangible devices which preferably include one or more machine-readable medium on which is stored one or more sets of instructions (e.g., software) embodying any one or more of the methodologies or functions described herein. The software may also reside, completely or at least partially, within the main memory, processor, or both during execution thereof by a computer within system, the main memory and the processor also constituting machine-readable media. The software may further be transmitted or received over a network via the network interface device.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. Memory may be, for example, one or more of a hard disk drive, solid state drive (SSD), an optical disc, flash memory, zip disk, tape drive, "cloud" storage location, or a combination thereof. In certain embodiments, a device of the invention includes a tangible, non-transitory computer readable medium for memory. Exemplary devices for use as memory include semiconductor memory devices, (e.g., EPROM, EEPROM, solid state drive (SSD), and flash memory devices e.g., SD, micro SD, SDXC, SDIO, SDHC cards); magnetic disks, (e.g., internal hard disks or removable disks); and optical disks (e.g., CD and DVD disks).

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of manufacturing a system for melting a thread to separate a neurovascular implant from a pusher, the method comprising:
   pinching a middle of a heater coil to a smaller diameter than at each of a distal end and a proximal end of the heater coil;
   with the middle of the heater coil pinched to the smaller diameter, pushing the distal end of the heater coil in a proximal direction over the the middle of the heater coil; and
   with the distal end of the heater coil pushed in the proximal direction over the middle of the heater coil, shrinking a first layer of an insulation jacket over the heater coil.

2. The method of claim 1, further comprising
   with the distal end of the heater coil pushed in the proximal direction over the middle of the heater coil, shrinking a second layer of the insulation jacket over the heater coil.

3. The method of claim 1, wherein pushing the distal end of the heater coil in the proximal direction over the middle of the heater coil includes moving the distal end of the heater coil coaxially relative to the middle of the heater coil.

4. The method of claim 1, further comprising positioning the heater coil relative to a stretch resistant thread such that the stretch resistant thread is rupturable via heat delivered to the distal end of the heater coil.

* * * * *